(12) United States Patent
Lytvynenko et al.

(10) Patent No.: US 10,126,261 B2
(45) Date of Patent: *Nov. 13, 2018

(54) METHOD AND DEVICE FOR CHARACTERISING A FLUID MEDIUM USING A SEMI-CONDUCTIVE SUBSTRATE

(71) Applicants: CENTRE NATIONAL DE LA RECHERCHE SCIENTIFIQUE, Paris (FR); ECOLE CENTRALE DE LYON, Ecully (FR); INSTITUT NATIONAL DES SCIENCES APPLIQUEES DE LYON, Villeurbanne (FR); UNIVERSITE CLAUDE BERNARD LYON I, Villeurbanne (FR); UNIVERSITE T. CHEVTCHENKO DE KIEV, Kiev (UA)

(72) Inventors: Sergeii Lytvynenko, Kiev (UA); Sergei Alexandrovich Alekseyev, Kiev (UA); Volodymyr Lysenko, Villeurbanne (FR); Valeriy Skryshevskyy, Kiev (UA)

(73) Assignees: CENTRE NATIONAL DE LA RECHERCHE SCIENTIFIQUE, Paris (FR); ECOLE CENTRALE DE LYON, Ecully (FR); INSTITUT NATIONAL DES SCIENCES APPLIQUEES DE LYON, Villeurbanne (FR); UNIVERSITE CLAUDE BERNARD LYON I, Villeurbanne (FR); UNIVERSITE T. CHEVTCHENKO DE KIEV, Kiev (UA)

( * ) Notice: Subject to any disclaimer, the term of this patent is extended or adjusted under 35 U.S.C. 154(b) by 402 days.

This patent is subject to a terminal disclaimer.

(21) Appl. No.: 14/654,605

(22) PCT Filed: Dec. 17, 2013

(86) PCT No.: PCT/FR2013/053134
§ 371 (c)(1),
(2) Date: Jun. 22, 2015

(87) PCT Pub. No.: WO2014/102484
PCT Pub. Date: Jul. 3, 2014

(65) Prior Publication Data
US 2015/0355125 A1    Dec. 10, 2015

(30) Foreign Application Priority Data

Dec. 27, 2012    (FR) ...................................... 12 62879

(51) Int. Cl.
*G01N 27/22*        (2006.01)
*G01N 33/00*        (2006.01)
(Continued)

(52) U.S. Cl.
CPC ........... *G01N 27/228* (2013.01); *G01N 22/00* (2013.01); *G01N 27/221* (2013.01);
(Continued)

(58) Field of Classification Search
CPC ............ G01N 27/228; G01N 33/0047; G01N 27/221; G01N 2027/222; G01N 21/1717;
(Continued)

(56) References Cited

U.S. PATENT DOCUMENTS

5,334,941 A * 8/1994 King ...................... G01N 22/00
324/637
6,783,993 B1 * 8/2004 Malmquist ............ B01F 9/0003
422/401

(Continued)

FOREIGN PATENT DOCUMENTS

EP    2 037 288     3/2009
WO   94/14188      6/1994

OTHER PUBLICATIONS

Wagner T. et al., "A high-density . . . FPGA control", Procedia Chemistry, vol. 1, No. 1, Sep. 1, 2009, pp. 1483-1486.

(Continued)

*Primary Examiner* — Sang Nguyen
(74) *Attorney, Agent, or Firm* — Clark & Brody (57) ABSTRACT

A method to determine an electronic signature characteristic of a fluid medium comprises making a reception surface for receiving the fluid medium on at least one face of the substrate, putting the fluid medium into contact with the reception surface in order to make an interface between the substrate and the fluid medium, lighting at least one zone of the interface through the fluid medium with a pulsed light beam in order to create photogenerated electric charges, using a microwave reflectometer to measure the lifetime durations of the photogenerated electric charges, which durations have respective values that depend on the recombination rate at the interface between the substrate and the fluid medium, creating a matrix of measured lifetime duration values for the photogenerated electric charges, and using the matrix to determine the electronic signature characteristic of the fluid medium.

11 Claims, 4 Drawing Sheets

(51) Int. Cl.
G01N 22/00 (2006.01)
G01N 21/17 (2006.01)

(52) U.S. Cl.
CPC . *G01N 33/0047* (2013.01); *G01N 2021/1719* (2013.01); *G01N 2027/222* (2013.01)

(58) Field of Classification Search
CPC .......... G01N 21/31; G01N 2021/1719; G01N 2201/061
See application file for complete search history.

(56) References Cited

U.S. PATENT DOCUMENTS

| | | | |
|---|---|---|---|
| 9,609,732 B2* | 3/2017 | Smith | B82Y 10/00 |
| 2002/0177961 A1* | 11/2002 | Lovegren | G01S 13/88 702/50 |
| 2009/0204346 A1* | 8/2009 | Xie | G01F 1/66 702/45 |
| 2013/0009048 A1* | 1/2013 | Xie | G01N 21/33 250/256 |
| 2015/0316470 A1* | 11/2015 | Lytvynenko | G01N 21/1717 356/440 |

OTHER PUBLICATIONS

Wagner et al., "A high-density multi-point . . . array and FPGA control", Science and Actuators B: Chemical, 2011, pp. 124-128.
James et al., "Chemical Sensors for Electronic Nose Systems", Microchm Acta 149, pp. 1-17, 2005.
Wagner et al., "A high-density multi-point . . . array and FPGA control", Procedia Chemistry 1, 2009, pp. 1483-1486.

* cited by examiner

METHOD AND DEVICE FOR CHARACTERISING A FLUID MEDIUM USING A SEMI-CONDUCTIVE SUBSTRATE

FIELD OF THE INVENTION

The present invention relates to the technical field of recognizing or characterizing a fluid medium in the general sense, with the help of a semiconductor substrate.

BACKGROUND ART

There are numerous applications for identifying fluid media and/or products or substances contained in fluid media, such as for example detecting products or substances in a fluid medium, quality control, or compliance checking, etc.

In the state of the art, the publication "A high density multipoint LAPS setup using VCSEL array and FPGA control" Sensors and Actuators B154 (2011), pp. 124-128, discloses a sensor known by the acronym L.A.P.S. (for light-addressable potentiometer sensor), of structure that comprises a potentiometer transducer in contact with the liquids for analysis and separated from a semiconductor element by an insulator. A modulated light source is used to create localized photon excitation that penetrates directly into the interior of the semiconductor element in order to generate electron-hole pairs in said element. A bias voltage applied to the terminals of the sensor leads to a photocurrent being generated. The value of the photocurrent depends in particular on the bias voltage, on the photon excitation, and on the potential of the interface between the liquid and the insulator.

It stems from the principle on which that sensor is based that the photocurrent signal is of a photocapacitive nature because of the interface between the insulator and the semiconductor. As a result, the sensitivity of such a sensor is low and the detected signal is of low power. Furthermore, it is found that the zones that are not lighted have an influence on the signal created by the localized zones that are lighted.

Also known in the state of the art is the publication "Chemical sensors for electronic nose systems", Microchim. Act 1.49, pp. 1-17 (2005), which discloses an electronic nose system using a chemical sensor for analyzing volatile organic compounds. Such a system has a metal oxide semiconductor field effect transistor (MOSFET). The grid of the transistor is in contact with the gas for analysis and is separated from the drain-source junction by an insulator. Charges on the insulator influence the drain-source current by means of a field effect and consequently influence the photocurrent picked up across the terminals of the transistor, thus enabling the gas for analysis to be characterized.

It stems from the principle of that electronic nose that the current signal between the drain and the source is modulated by the field effect via the interface between the insulator and the fluid. A drawback of that electronic nose lies in the need to have a specific grid in order to characterize gases selectively. In this respect, and by way of example, in order to be sensitive to compounds that are neutral, it is necessary to use specific catalysts so as to decompose the neutral molecules into charged elements. Another drawback of that electronic nose (from the point of view of technologically implementing it) lies in the need for the drain and the source of each transistor to be electrically insulated from the fluid for analysis. The spatial resolution of that device is defined and limited by the size of each transistor.

In the technical field seeking to determine the purity of semiconductor materials and examining the lifetimes of minority carriers, it is known to use a microwave measurement technique associated with a pulsed laser source. For example, in order to measure the lifetimes of minority carriers of a semiconductor substrate, Document WO 94/14188 proposes surrounding the semiconductor substrate with a passivation solution and subjecting it to a microwave source and to a pulsed light source in order to create photogenerated electric charges. The reflective microwave energy is detected, thus making it possible to measure the lifetime durations of the photogenerated electric charges. On the basis of that measurement, it is therefore possible to detect defects in the semiconductor substrate.

SUMMARY OF THE INVENTION

The present invention seeks to remedy the drawbacks of the prior art by proposing a novel method using a semiconductor substrate to characterize a fluid medium, i.e. a liquid and/or a gas and/or products or substances contained in fluid media, which medium may optionally be electrically neutral, the characterization method presenting high sensitivity and spatial resolution that is easily adaptable.

In order to achieve such an object, the invention proposes a method of characterizing a fluid medium with the help of a semiconductor substrate.

According to the invention, the method comprises the following steps:

making a reception surface for receiving the fluid medium on at least one face of the substrate;

putting the fluid medium for characterizing into contact with the reception surface in order to make an interface between the substrate and the fluid medium;

lighting at least one zone of the interface through the fluid medium with the help of a pulsed light beam in order to create photogenerated electric charges;

using a microwave reflectometer to measure the lifetime durations of the photogenerated electric charges, which durations have respective values that depend on the recombination rate at the interface between the substrate and the fluid medium;

creating a matrix of measured lifetime duration values for the photogenerated electric charges;

using the matrix that has been created of lifetime durations to determine an electronic signature characteristic of the fluid medium; and analyzing the electronic signature in order to recognize the fluid medium (3) and/or one or more of its individual components.

Furthermore, the method of the invention may also present in combination at least one and/or more of the following additional characteristics:

lighting a plurality of zones of the interface successively over time and in determining the corresponding lifetime durations for the photogenerated electric charges for at least each lighted zone in order to create a one- or two-dimensional matrix of lifetime duration values;

lighting the interface zone with pulsed light flux coming from at least a single light beam of position relative to the substrate that can be changed;

changing the position of the pulsed light beam relative to the zone of the interface, in a manner that is discrete or continuous;

renewing the steps of lighting, measuring lifetime durations, creating the matrix, and determining the electronic signature, while modifying one or more of the following experimental parameters: lighting intensity; lighting area; lighting wavelength; temperature of the fluid medium and/or of the substrate; intensity of the external electric field applied to the interface between the substrate and the fluid medium; and a voltage applied between the electrodes in electrical contact with the fluid medium and with the substrate;

determining as the electronic signature characteristic of the fluid medium at least one visual image of the interface between the substrate and the fluid medium, and for at least one value of at least one experimental parameter;

subdividing the field over which the measured lifetime duration values vary into areas, each of which has a color allocated thereto so that the electronic signature is a color image;

the step of analyzing the signature consists in comparing the electronic signature of the fluid medium with at least one reference electronic signature determined for a known fluid medium;

the step of analyzing the signature consists in using quantitative methods for processing the images obtained; and performing a step of treating the reception surface prior to performing the lighting step.

The invention also proposes a system for characterizing a fluid medium with the help of a semiconductor substrate.

According to the invention, the system comprises:

at least one reception surface on the substrate for receiving the fluid medium in order to constitute an interface between the substrate and the fluid medium;

a production system for producing at least one pulsed spot light beam for lighting at least one zone of the interface between the substrate and the fluid medium through the fluid medium in order to create photogenerated electric charges presenting lifetime durations of respective values that depend on rate of recombination at the interface after extinction of the light pulse;

a microwave source;

an antenna coupled to the source and designed to direct the microwaves towards the interface between the substrate and the fluid;

a detector coupled to the antenna in order to detect microwaves that are reflected by the photogenerated electric charges;

a determination system responsive to the reflected microwaves to determine the lifetime durations in order to create a matrix of lifetime duration values; and a processor system for processing lifetime duration values and adapted to use the matrix to establish an electronic signature characteristic of the fluid medium and to analyze the electronic signature in order to recognize the fluid medium and/or one or more of its individual components.

Furthermore, the system of the invention may also include in combination at least one and/or more of the following additional characteristics:

a control system for controlling the spot light beam relative to the interface between the substrate and the fluid in such a manner as to light a plurality of interface zones so as to measure lifetime duration values for photogenerated electric charges at each of the lighted interface zones; and the production system for producing the spot light beam comprises a spot light source associated with a system for moving the beam relative to the interface between the substrate and the fluid.

BRIEF DESCRIPTION OF THE DRAWINGS

Various other characteristics appear from the following description made with reference to the accompanying drawings, which show implementations of the invention as non-limiting examples.

DETAILED DESCRIPTION OF THE INVENTION

Figure 1:
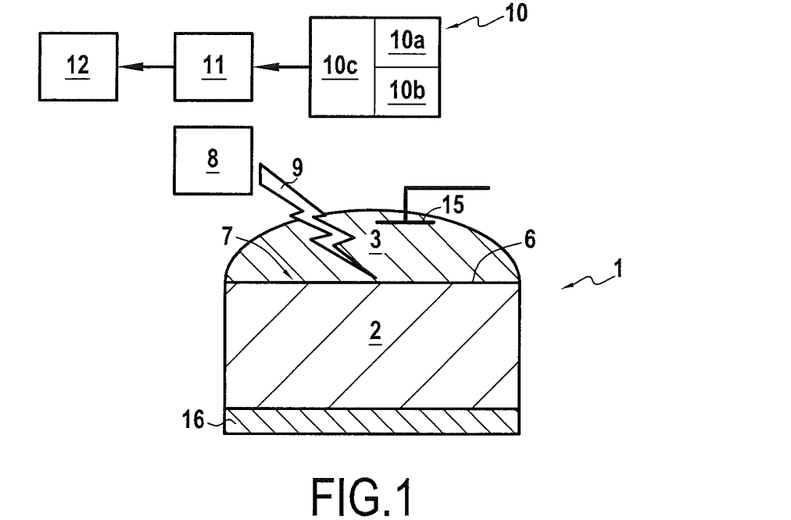
FIG. 1 is an elevation view in section showing the general principle of the invention.

FIG. 1 shows the principle of a device 1 in accordance with the invention suitable for characterizing a fluid medium 3 in the general sense with the help of a semiconductor substrate 2. In the meaning of the invention, a fluid medium is a liquid, a gas, or a gaseous liquid, of homogeneous or heterogeneous nature, i.e. containing various substances, products, or compounds such as, by way of example: biological objects (bacteria, cells, viruses, proteins, etc.) or particles in the solid state that may be suspended or dissolved in the liquid media or evaporated in the form of a gas. The term "characterizing" is thus used for the fluid medium to mean identifying at least one specific compound forming the fluid medium or contained in the fluid medium. As non-limiting examples, it is possible to use as the fluid medium food industry products, cosmetics, fragrances, biomedical products, hydrocarbons, drugs, explosive substances, . . . .

The semiconductor substrate 2 has a reception surface 6 for the fluid medium 3 in order to constitute an interface 7 between the substrate 2 and the fluid medium 3. By way of example, the semiconductor substrate 2 is constituted by a standard silicon substrate of microelectronic quality without any special treatment. For example, the reception surface 6 of the semiconductor substrate 2 may be naturally oxidized in air.

The device 1 of the invention also has a production system 8 for producing a pulsed spot light beam 9 and adapted to light at least one zone of the interface 7 through the fluid medium 3. The production system 8 is controlled to light a zone of the interface 7 for a determined duration. The production system 8 is adapted to illuminate one or more zones of the interface 7 after passing through the fluid medium 3 by using a pulsed light beam.

The production system 8 is made in any appropriate manner and may, by way of example, comprise a point light source or an array of light-emitting diodes (LEDs) with on/off control.

In a variant embodiment, the device 1 has a system for controlling the spot light beam so as to light a plurality of zones of the interface. In particular, the system for controlling the spot light beam has a system for moving the system for producing the spot light beam so as to be capable of illuminating different zones of the interface 7 in discrete or continuous manner.

In another variant embodiment, the production system 8 has an array of LEDs distributed over a zone and subjected to selective on/off control so as to light a plurality of different zones of the interface 7.

The system 8 thus produces light pulses 9 for lighting one or more zones of the interface 7 through the fluid medium 3 so as to create photogenerated electric charges in the semiconductor substrate 2.

The device 1 of the invention also has a microwave reflectometer 10 for measuring the lifetime of the electric charges that are photogenerated while illuminating the semiconductor substrate 2. The microwave reflectometer 10 may be of any known type. Conventionally, the reflectometer 10 comprises a microwave source 10a coupled to an antenna 10b that is designed to direct the microwaves towards the interface 7 between the substrate 2 and the fluid medium 3, and more precisely at least in the zone of the interface 7 that is lighted by the light beam 9. The reflectometer 10 also has a detector 10c coupled to the antenna 10b in order to detect the microwaves that are reflected by the electric charges photogenerated during illumination of the semiconductor substrate 2. The detector 10c thus measures the microwave reflection induced by the photogenerated electric charges. The detector 10c is connected to a measurement system 11 suitable for determining on the basis of the reflected microwaves the duration of the lifetime of these electric charges and to create a matrix of measured lifetime durations.

Figure 2A:
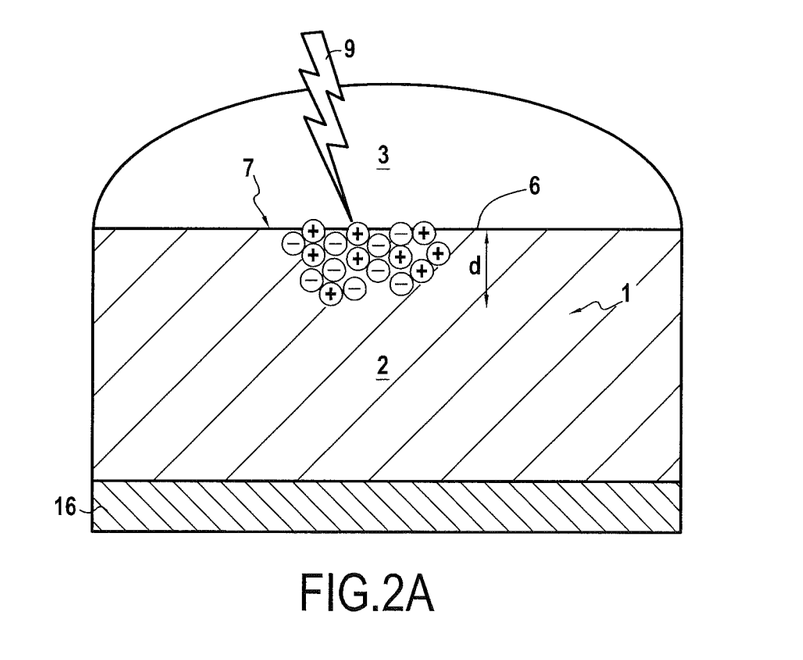
FIGS. 2A and 2B serve to illustrate the mechanism for measuring the lifetimes of generated photoelectric charges.
Figure 2B:
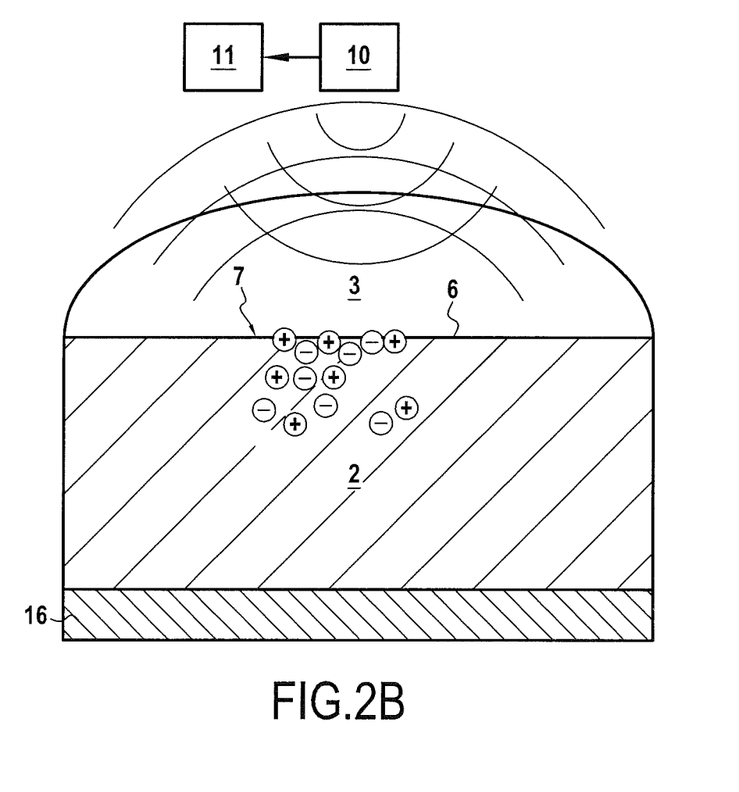

FIGS. 2A and 2B show the mechanism for measuring the lifetime duration of photogenerated electric charges.

As shown in FIG. 2A, a fluid medium 3 is put into contact with the surface 6 of the semiconductor substrate 2 in order to provide the substrate and fluid medium interface 7. Lighting a zone of the interface 7 through the fluid medium 3 for a determined length of time leads to electric charges (electrons $e^-$ and holes $e^+$) being created inside the semiconductor substrate 2 and from the interface 7. It should be observed that the depth $\underline{d}$ at which electric charges are generated inside the semiconductor substrate 2 depends in particular on the wavelength of the light beam 9 and on the physicochemical nature of the semiconductor substrate 2.

After electric charges have appeared inside the semiconductor substrate 2, and as shown in FIG. 2B, some of the photogenerated electric charges inevitably recombine. This recombination is a function of the electronic nature and the quality of the reception surface 6. This recombination of some of the photogenerated electric charges is characterized by its recombination speed. It should be understood that the photogenerated electric charges thus present a lifetime between their appearance and their recombination. Thus, variation in the concentration of photogenerated electric charges over time as a result of recombination at the interface 7 depends on the lifetime durations of the charges.

The microwave reflectometer 10 is used to measure the lifetime durations of the electric charges photogenerated while lighting the interface 7 through the fluid medium 3. For this purpose, microwave radiation in the radiofrequency (RF) spectrum range is sent to the interface 7 so that a portion of the radiation is reflected by the photogenerated electric charges. For example, the microwave radiation is sent to the interface (FIG. 2B) after extinction of the light pulse 9. Recovering the reflected microwave radiation then makes it possible to determine the lifetime durations of the photogenerated electric charges.

On each occasion a zone of the interface 7 is lighted, the system 11 thus uses the reflectometer 10 to measure the values of the lifetime durations of the photogenerated photoelectric charges.

It can be seen from the above-described principle that the measured values for lifetime durations after lighting the interface 7 are defined directly by the rate at which the photogenerated electric charges recombine, which rate depends on the characteristics of the lighted interface zone 7. It is possible to obtain high measurement sensitivity over a wide range of values for measured lifetime durations insofar as the recombination rate can vary over several orders of magnitude (e.g. in the range $10^2$ centimeters per second (cm/s) to $10^6$ cm/s).

The spatial resolution of the measurement, which is responsible for the quality of the recognition or of the characterization of the fluid medium and which defines the minimum area value for the reception surface 6 depends on the size of the light spot 9, i.e. on the area of the lighted zone of the interface 7. The spatial resolution of the measurement also depends on the minimum movement of the light spot for which it is possible to detect a change in lifetime duration. In other words, the spatial resolution depends on the degree of heterogeneity in the rate of recombination at the reception surface 6.

In an aspect of the invention, it is found advantageous to characterize a fluid medium by lighting a plurality of different zones of the interface 7 that present different lifetime durations, either naturally or as a result of special treatment. Specifically, it has been observed that the interface 7 naturally presents different rates of recombination that are spread over the surface of the interface 7. Of course, it is possible to envisage applying treatment, e.g. chemical treatments, to the reception surface 6 in order to obtain different recombination rates that are selectively distributed over the reception surface 6. By way of example, it is possible to envisage the following treatments for chemically treating the reception surface of the substrate:

oxidizing, nitriding, carbonizing, or porosification of the initial substrate;

depositing layers of oxides, nitrides, carbides, or various porous layers on the surface of the substrate;

chemically grafting organic functional groups by hydrosilylation (e.g. a fresh Si surface);

chemically grafting organic functional groups by silanization (e.g. an oxidized or nitrided Si surface);

electrochemically grafting organic functional groups;

grafting organic functional groups with alcohols or amines;

consecutive reconstructions of the surface of the substrate with organic functional groups;

filling pores of porous layers with polymers, nanoparticles (carbon, semiconductor, or metal nanoparticles), or water-insoluble weakly-polar liquids; and within the pores or on the surface 6 of the substrate 2, growing layers or membranes that are selectively sensitive to the ions and ionophoric solutions in the polymers.

The presence of different recombination rates at the interface 7 makes it possible to create a matrix of lifetime duration values.

In a preferred variant embodiment, the measurement system 11 also stores the measured values for lifetime durations in order to create a matrix of values corresponding to the lifetime duration values measured for the various illuminated zones of the interface 7. For this purpose, the measurement system 11 includes any known type of storage means.

The dimension of this matrix of values depends on the number of illuminated zones and/or on the number of external parameters that are defined and controlled while taking the measurements, such as for example: time, temperature, lighting conditions, electric field, etc. By way of example, when lighting a single zone while keeping the external measurement parameters constant, the matrix has only one value. When lighting n interface zones 7 distributed along a direction of the interface 7 and when keeping the external measurement parameters constant, a one-dimensional matrix is obtained. When lighting n interface zones 7 that are distributed in rows and columns (where n is greater than 1) and when keeping external measurement parameters constant, the matrix of n values has two dimensions.

The device 1 of the invention also has a processor system 12 for processing lifetime duration values delivered by the measurement system 11. The processor system 12 is adapted to use the matrix of lifetime duration values in order to determine a fingerprint or an electronic signature that is characteristic of the fluid medium. In other words, the processor system 12 serves to characterize the fluid medium from the measured lifetime duration values.

The processor system 12 makes use of various methods for characterizing the fluid medium on the basis of the measured lifetime duration values. A simplified method consists in characterizing the fluid medium directly from the measured values of lifetime duration. In an advantageous variant embodiment, the measured values of lifetime duration are represented in the form of an image. In this variant, the matrix of lifetime duration values is converted into or represented in the form of an image having one or more colors and possibly shades of the colors. Thus, the field over which the lifetime duration values vary is subdivided into a plurality of areas with a color or a color shade being allocated to each of them so that a two-dimensional matrix of values gives rise to an image of corresponding colors that is likewise of two dimensions.

Figure 3A:
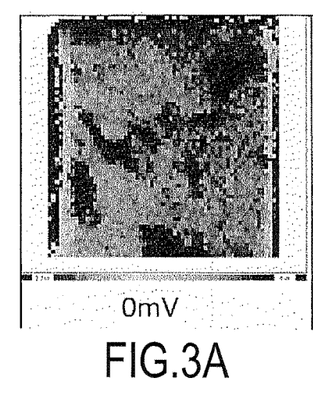
FIGS. 3A to 3G are examples of images obtained from matrices of values measured for water as the fluid medium, for various bias voltages.
Figure 3B:
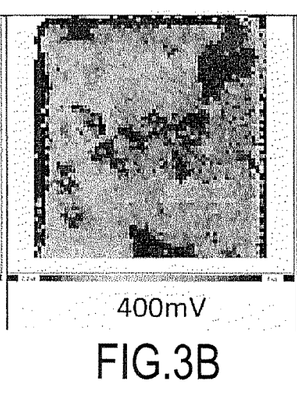
Figure 3C:
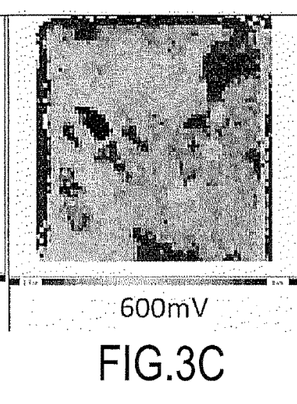
Figure 3D:
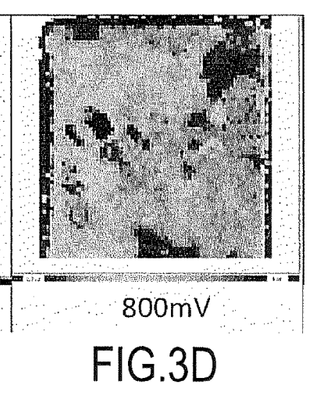
Figure 3E:
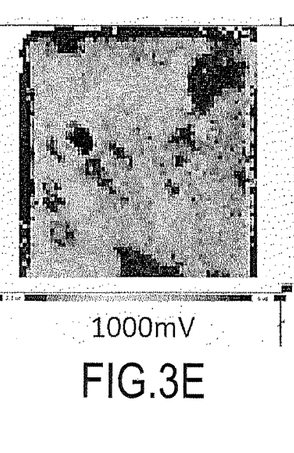
Figure 3F:
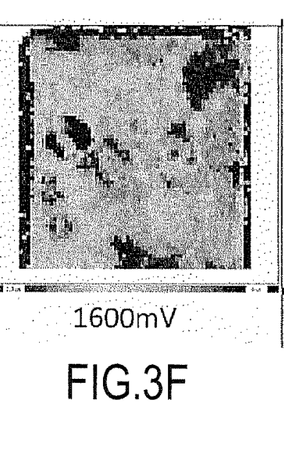
Figure 3G:
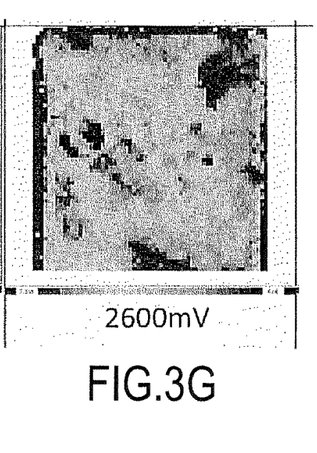
Figure 4A:
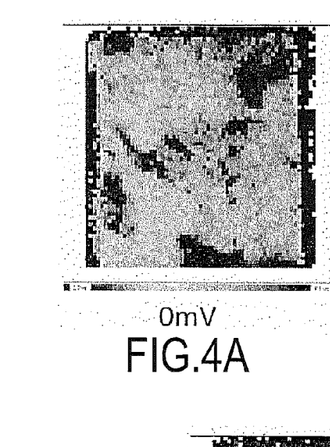
FIGS. 4A to 4G are examples of images obtained from matrices of values measured with ethanol as the fluid medium, for various bias voltages.
Figure 4B:
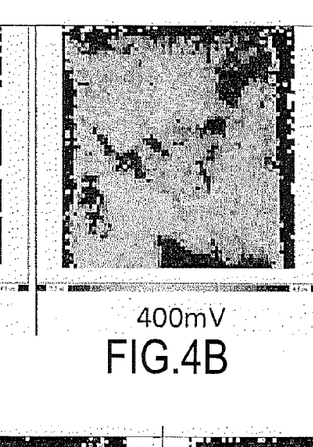
Figure 4C:
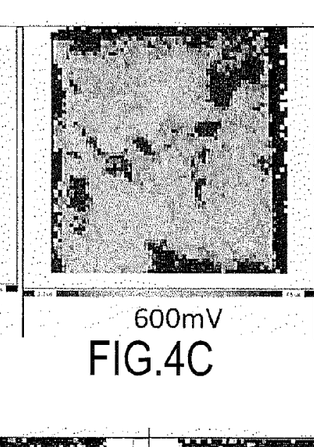
Figure 4D:
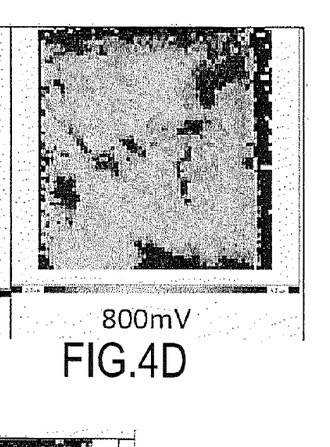
Figure 4E:
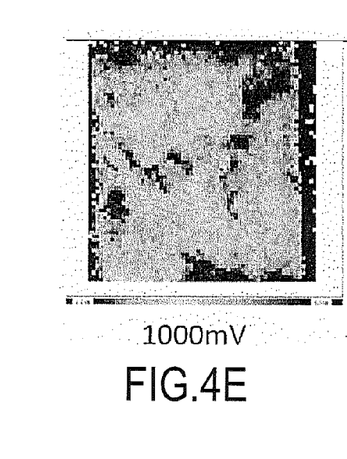
Figure 4F:
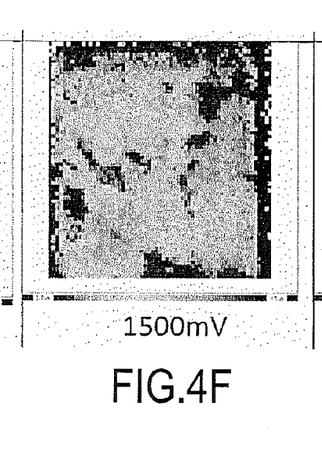
Figure 4G:
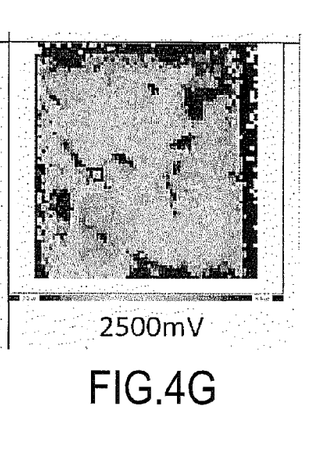

FIGS. 3A and 4A are examples of images obtained from a matrix of lifetime duration values for photogenerated electric charges as measured respectively with water and with ethanol as the fluid medium with a bias voltage value equal to 0 millivolts (mV). The palest zones in the images correspond to the greatest values in the matrix.

The description below gives other examples serving to illustrate the method of the invention which is performed essentially in several variant implementations.

In a first variant implementation, the semiconductor substrate 2 has a first electrode 15 immersed in the fluid medium 3 and a second electrode 16 made on the face of the semiconductor substrate opposite from its face forming the interface 7. The electrodes 15, 16 are connected to an electrical power supply suitable for applying a bias voltage to the assembly comprising the fluid medium 3 and the semiconductor substrate 2.

Advantageously, the invention seeks to create lifetime duration matrices and consequently electronic signatures for different values of the voltage applied between the electrodes 15 and 16.

FIGS. 3A to 3G show an example of images obtained from the lifetime durations of photogenerated electric charges as measured for water with the following respective values for the bias voltage: 0 mV, 400 mV, 600 mV, 800 mV, 1000 mV, 1600 mV, and 2600 mV.

FIGS. 4A to 4G show an example of images obtained from the lifetime durations of photogenerated electric charges as measured for ethanol with the following respective values for the bias voltage: 0 mV, 400 mV, 600 mV, 800 mV, 1000 mV, 1600 mV, and 2500 mV.

It can be seen from the above description that the device 1 of the invention serves to characterize or identify a fluid medium from lifetime duration values of electric charges that are characteristic of said fluid medium. The method of identifying a fluid medium stems directly from the above description.

The method of the invention thus consists in:
making a reception surface 6 on the substrate 2 for receiving the fluid medium 3 on at least one face of the substrate;
putting the fluid medium 3 for characterizing into contact with the reception surface so as to provide an interface 7 between the substrate and the fluid medium;
lighting at least one zone of the substrate through the fluid medium 3 with the help of a pulsed light beam so as to create photogenerated electric charges;
using a microwave reflectometer 10 for measuring the lifetime durations of the photogenerated electric charges, which durations have respective values that depend on the recombination rate at the interface 7 between the substrate and the fluid medium;
creating a matrix of measured lifetime duration values for the photogenerated electric charges;
from the matrix that has been created of lifetime durations, determining an electronic signature that is characteristic of the fluid medium; and
analyzing the electronic signature in order to recognize the fluid medium 3 and/or one or more of its individual components.

It should be understood that the method of the invention makes it possible to identify a fluid medium from the matrix of lifetime duration values for the photogenerated electric charges, which matrix forms a unique electronic signature for each fluid medium. Naturally, in order to increase the quality of detection, the detection method consists in renewing the steps of lighting, recovering lifetime duration values, creating the matrix, and determining the electronic signature, either while maintaining various experimental parameters constant or while modifying one and/or more of the following experimental parameters: lighting intensity; lighting area; lighting wavelength; temperature of the fluid medium and/or of the substrate; intensity of the external electric field applied to the interface between the substrate and the fluid medium; and a voltage applied between the electrodes in electrical contact with the substrate 2 and the fluid medium 3.

This electronic signature is preferably converted into a visual image. The fluid medium can be identified from one or more images using the naked eye, by comparison with a reference electronic signature determined for a known fluid medium, or with the help of various kinds of image processing, and in particular by using quantitative methods for processing the resulting images. The electronic signature is analyzed in order to recognize the fluid medium 3 and/or one or more of its individual components.

The invention is not limited to the examples described and shown since various modifications may be applied thereto without going beyond its ambit.

The invention claimed is:
1. A method of characterizing a fluid medium, the method comprising the following steps:
making a reception surface for receiving the fluid medium on at least one face of the substrate;
putting the fluid medium into contact with the reception surface in order to make an interface between the substrate and the fluid medium;
using a production system for producing a pulsed light beam to illuminate at least one zone of the interface through the fluid medium with the help of the pulsed light beam in order to create photogenerated electric charges;

using a microwave reflectometer to measure lifetime durations of the photogenerated electric charges, which lifetime durations have respective values that depend on a recombination rate at the interface between the substrate and the fluid medium; and using the microwave reflectometer to create a matrix of measured lifetime duration values for the photogenerated electric charges;

using a processor system to determine an electronic signature that is characteristic of the fluid medium from the lifetime duration matrix that has been created; and using the processor system to analyze the electronic signature in order to recognize the fluid medium, one or more of individual components of the fluid medium, or a combination thereof.

2. A method according to claim 1, further comprising lighting a plurality of zones of the interface successively over time and in determining the corresponding lifetime durations for the photogenerated electric charges for at least each lighted zone in order to create a one- or two-dimensional matrix of lifetime duration values.

3. A method according to claim 1, further comprising lighting the interface zone with pulsed light flux coming from at least a single light beam of position relative to the substrate that can be changed.

4. A method according to claim 1, further comprising changing a position of the pulsed light beam relative to the zone of the interface, in a manner that is discrete or continuous.

5. A method according to claim 1, further comprising renewing the steps of lighting, measuring lifetime durations, creating the matrix, and determining the electronic signature, while modifying one or more of the following experimental parameters: lighting intensity; lighting area; lighting wavelength; temperature of the fluid medium and/or of the substrate; intensity of the external electric field applied to the interface between the substrate and the fluid medium; and a voltage applied between the electrodes in electrical contact with the fluid medium and with the substrate.

6. A method according to claim 5, further comprising determining as the electronic signature characteristic of the fluid medium at least one visual image of the interface between the substrate and the fluid medium, and for at least one value of at least one experimental parameter.

7. A method according to claim 1, further comprising subdividing a field over which the measured lifetime duration values vary into areas, each of which has a color allocated thereto so that the electronic signature is a color image.

8. A method according to claim 1, wherein the step of analyzing the electronic signature comprises comparing the electronic signature of the fluid medium with at least one reference electronic signature determined for a known fluid medium.

9. A method according to claim 1, wherein the step of analyzing the electronic signature comprises using quantitative methods for processing the images obtained.

10. A method according to claim 1, further comprising performing a step of treating the reception surface prior to performing the lighting step.

11. A system for characterizing a fluid medium with the help of a semiconductor substrate, the system comprising:

at least one reception surface on the substrate for receiving the fluid medium in order to constitute an interface between the substrate and the fluid medium;

a production system for producing at least one pulsed spot light beam for lighting at least one zone of the interface between the substrate and the fluid medium through the fluid medium in order to create photogenerated electric charges presenting lifetime durations of respective values that depend on rate of recombination at the interface after extinction of the light pulse;

a microwave source;

an antenna coupled to the microwave source and designed to direct the microwaves towards the interface between the substrate and the fluid;

a detector coupled to the antenna in order to detect microwaves that are reflected by the photogenerated electric charges;

a determination system responsive to the reflected microwaves to determine the lifetime durations in order to create a matrix of lifetime duration values; and a processor system for processing lifetime duration values and adapted to use the matrix to establish an electronic signature characteristic of the fluid medium and to analyze the electronic signature in order to recognize the fluid medium, one or more of individual components of the fluid medium, or a combination thereof.

* * * * *